United States Patent
Lee et al.

(10) Patent No.: US 8,625,090 B2
(45) Date of Patent: Jan. 7, 2014

(54) METHOD AND APPARATUS FOR INSPECTING SUBSTRATES

(75) Inventors: Moon-kyu Lee, Seoul (KR); Cheongsoo Kim, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 192 days.

(21) Appl. No.: 13/226,102

(22) Filed: Sep. 6, 2011

(65) Prior Publication Data

US 2012/0069330 A1    Mar. 22, 2012

(30) Foreign Application Priority Data

Sep. 17, 2010    (KR) .................. 10-2010-0091997

(51) Int. Cl.
     *G01N 21/88*      (2006.01)
(52) U.S. Cl.
     USPC .................................................... 356/237.5
(58) Field of Classification Search
     USPC .......................................... 356/237.1–237.5
     See application file for complete search history.

(56) References Cited

U.S. PATENT DOCUMENTS

| | | | | |
|---|---|---|---|---|
| 5,907,398 | A * | 5/1999 | Fujino et al. ................ | 356/237.3 |
| 6,437,862 | B1 * | 8/2002 | Miyazaki et al. .......... | 356/237.2 |
| 7,075,637 | B2 * | 7/2006 | Leslie et al. ................ | 356/237.2 |
| 2004/0066507 | A1 * | 4/2004 | Kren et al. ................. | 356/237.4 |
| 2005/0018183 | A1 * | 1/2005 | Shortt ........................ | 356/239.1 |
| 2005/0094136 | A1 * | 5/2005 | Xu et al. .................... | 356/237.3 |
| 2007/0052955 | A1 * | 3/2007 | Shishido et al. ........... | 356/237.2 |
| 2010/0085561 | A1 * | 4/2010 | Kamiyama et al. ........ | 356/237.5 |

FOREIGN PATENT DOCUMENTS

| | | |
|---|---|---|
| KR | 10-2004-0008417 A | 1/2004 |
| KR | 10-2006-0024662 A | 3/2006 |
| KR | 10-2009-0095837 A | 9/2009 |
| KR | 10-0914971 B1 | 9/2009 |

\* cited by examiner

*Primary Examiner* — Hoa Pham
(74) *Attorney, Agent, or Firm* — Sughrue Mion, PLLC

(57) ABSTRACT

A method and an apparatus for inspecting a substrate are provided. The method includes irradiating light to a semiconductor device formed on a substrate and detecting light reflected from the semiconductor device in order to inspect a defect of the semiconductor device. An irradiation position of the light may gradually move from a semiconductor device formed at the center of the substrate to a semiconductor device formed on an edge of the substrate. at least one semiconductor device formed on a substrate, a light irradiating member which irradiates light onto the semiconductor surface formed on the substrate; a light detecting member which detects light reflected from the semiconductor device in order to inspect the semiconductor device for defects; and an irradiation position of the light gradually moves from a semiconductor device formed at the center of the substrate to a semiconductor device formed on an edge of the substrate.

13 Claims, 9 Drawing Sheets

METHOD AND APPARATUS FOR INSPECTING SUBSTRATES

CROSS-REFERENCE TO RELATED APPLICATIONS

This US non-provisional patent application claims priority under 35 USC §119 to Korean Patent Application No. 10-2010-0091997, filed on Sep. 17, 2010, the entirety of which is hereby incorporated by reference.

BACKGROUND

The inventive concept described herein generally relates to methods and apparatuses for inspecting substrates. More particularly, the inventive concept relates to methods and apparatuses for inspecting defects of semiconductor devices which are formed on a substrate.

As patterns become finer in accordance with recent trends toward high integration and high speed of semiconductor devices, minimization of pattern defects such as break of pattern, void, and bridge are key points for improving yield. The pattern defects are inspected from image data obtained by irradiating light on a substrate where a semiconductor device is formed and detecting light reflected from the substrate.

SUMMARY

Exemplary embodiments of the inventive concept provide a method and apparatus for inspecting a substrate. In an aspect of the inventive concept, the method may include irradiating light onto a semiconductor device formed on a substrate; and detecting light reflected from the semiconductor device, in order to inspect a defect of the semiconductor device. An irradiation position of the light may gradually move from a semiconductor device formed at the center of the substrate to a semiconductor device formed on the edge of the substrate.

According to one exemplary embodiment, the irradiation position of the light may sequentially move from a semiconductor device disposed along a center line of a plane of the substrate to semiconductor devices in a direction perpendicular to the center line.

According to one exemplary embodiment, the center line may be aligned along one of a plurality of arrangement directions of the semiconductor devices formed on the substrate.

According to one exemplary embodiment, the irradiation position of the light may move in at least one of first and second directions perpendicular to a center line of the substrate.

According to one exemplary embodiment, when the number of defects of the inspected semiconductor device exceeds a predetermined value, the other semiconductor devices disposed at the outside of the inspected semiconductor device may stop being inspected in a moving direction of the irradiation position of the light.

According to one exemplary embodiment, after stopping inspection of the other semiconductor devices, the irradiation position of the light may move from another semiconductor device disposed along the center line to semiconductor devices disposed in a direction perpendicular to the center line.

According to one exemplary embodiment, the substrate may include semiconductor devices where patterns are formed in different exposure conditions in order to detect more defects at the center portion of the substrate than at the edge portion of the substrate.

According to one exemplary embodiment, the exposure condition may include a focal length and/or exposure time.

According to one exemplary embodiment, the irradiation position of the light may sequentially move from a central semiconductor device disposed at the center of the substrate to semiconductor devices disposed on the edge of the substrate while making a quadrangular spiral.

According to one exemplary embodiment, location information of a semiconductor device whose inspected defects are greater than a predetermined value may be stored, and semiconductor devices disposed around the semiconductor device which is opposite to the semiconductor device whose location information is stored may not be inspected in one of horizontal and vertical directions of the quadrangular spiral.

According to one exemplary embodiment, the substrate may include the semiconductor device where patterns are formed in different exposure conditions in order to detect more defects at the edge portion of the substrate than at the center portion of the substrate.

In another aspect of the inventive concept, the method may include providing a substrate including semiconductor devices arranged in the form of a lattice and where patterns are formed under different exposure conditions, such that more defects are detected at a edge portion of the substrate than at an center portion of the substrate; sequentially irradiating light from a semiconductor device formed at the center portion of the substrate to a semiconductor device formed at the edge portion of the substrate; and detecting light reflected from the semiconductor devices in order to inspect defects of the semiconductor devices.

According to one exemplary embodiment, the light may be irradiated from the respective semiconductor devices linearly disposed in a first direction among arrangement directions of the semiconductor devices to the semiconductor devices disposed in a second direction.

According to one exemplary embodiment, when the number of defects of the inspected semiconductor device exceeds a predetermined value, the other semiconductor devices disposed at the outside of the inspected semiconductor device may stop being inspected in the second direction.

According to one exemplary embodiment, the inspection may be conducted from the semiconductor device disposed at the center of the substrate, from among the semiconductor devices linearly disposed in the first direction, to the semiconductor device disposed around the semiconductor device in a second direction.

According to one exemplary embodiment, the light may be sequentially irradiated from a central semiconductor device disposed at the center of the substrate to semiconductor devices disposed on the edge of the substrate, while making a quadrangular spiral.

According to one exemplary embodiment, location information of a semiconductor device whose inspected defects are greater than a predetermined value may be stored, and semiconductor devices disposed around the semiconductor device to be opposite from the semiconductor device whose location information is stored may not be inspected in one of horizontal and vertical directions of the quadrangular spiral.

Exemplary embodiments of the inventive concept provide an apparatus for inspecting a substrate. In an aspect of the inventive concept, the apparatus may include a substrate support member on which a substrate is placed; a light irradiation member irradiating light onto a semiconductor device formed on the substrate placed on the substrate support member; a light detection member receiving light reflected from the semiconductor device to detect a defect of the semiconductor device; a moving member moving the substrate support member in arrangement directions of the semiconductor device; and a controller controlling the moving member to gradually move an irradiation position of the light from a semiconductor device formed at a center portion of the substrate to a semiconductor device formed at an edge portion of the substrate.

According to one exemplary embodiment, the controller may control the moving member to irradiate light from the semiconductor devices linearly disposed in a first direction from among arrangement directions of the semiconductor devices to the semiconductor devices disposed in a second direction.

According to one exemplary embodiment, the controller may control the moving member in order to irradiate light from a central semiconductor device disposed at the center of the substrate to semiconductor devices disposed on the edge of the substrate, while making a quadrangular spiral.

BRIEF DESCRIPTION OF THE DRAWINGS

The inventive concept will become more apparent in view of the attached drawings and accompanying detailed description. The exemplary embodiments depicted therein are provided by way of example, not by way of limitation, wherein like reference numerals refer to the same or similar elements. The drawings are not necessarily to scale, with emphasis instead being placed upon illustrating aspects of the exemplary embodiments.

DETAILED DESCRIPTION

The inventive concept will now be described with reference to the accompanying drawings, in which exemplary embodiments of the inventive concept are shown. However, the inventive concept may be embodied in many different forms and should not be construed as limited to the exemplary embodiments set forth herein. Rather, these exemplary embodiments are provided so that this disclosure will be thorough and complete, and will fully convey the scope of the inventive concept to those skilled in the art. Like numbers refer to like elements throughout.

A substrate inspecting apparatus according to exemplary embodiments of the inventive concept irradiate light on a pattern surface of a substrate (e.g., semiconductor wafer), detect light reflected from the pattern surface in order to obtain an image of the pattern surface, and inspects particles or pattern defects (e.g., break of pattern, bridge, void, etc.) on the pattern surface, from data obtained from the image.

Figure 1:
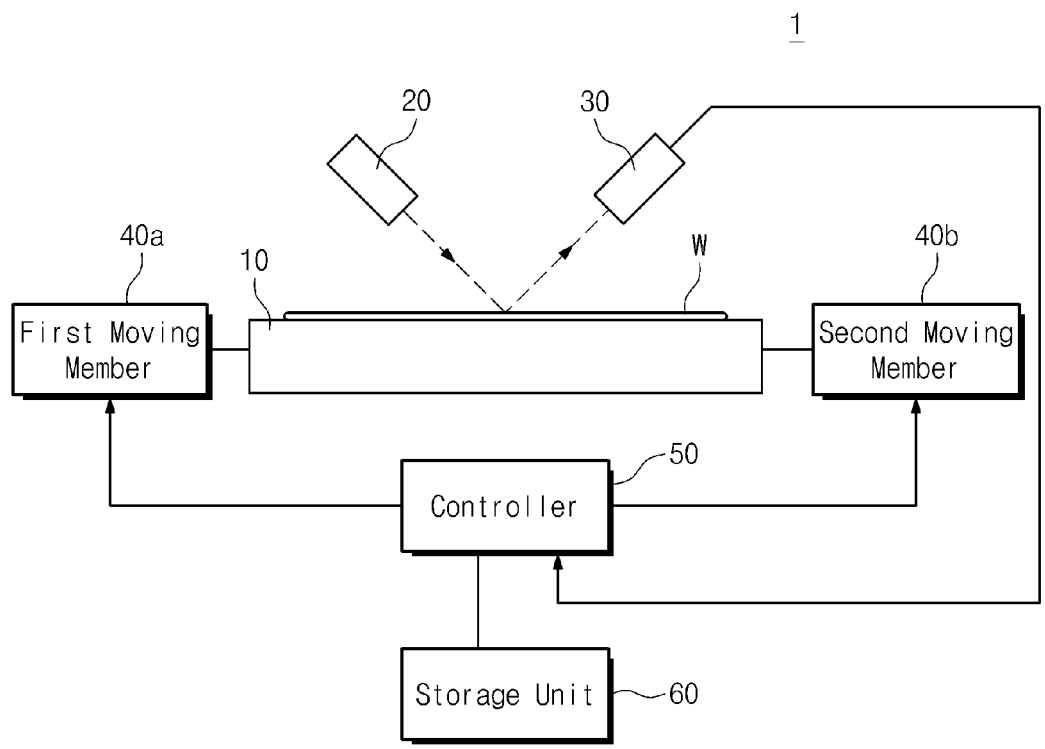
FIG. 1 is a side view of a substrate inspection apparatus according to an exemplary embodiment.
Figure 2:
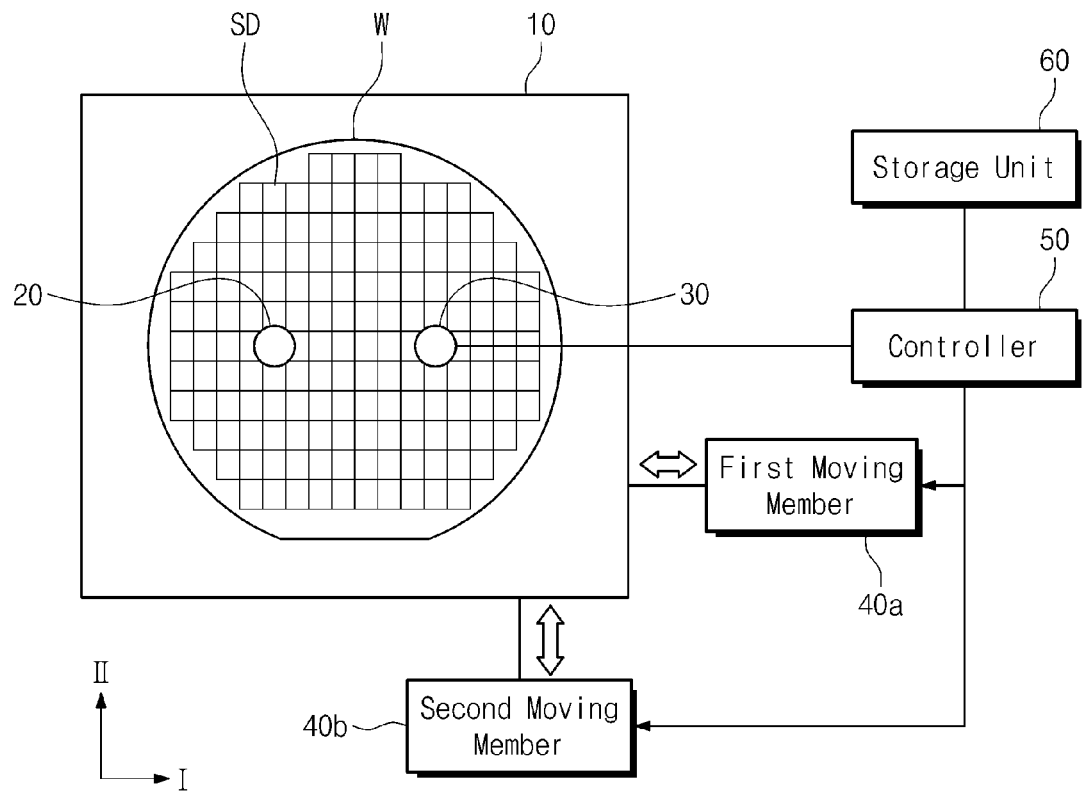
FIG. 2 is a top plan view of a substrate inspection apparatus according to an exemplary embodiment.

FIGS. 1 and 2 represent a side view and a top plan view, respectively of a substrate inspecting apparatus 1, according to an exemplary embodiment of the inventive concept. As illustrated, substrate inspecting apparatus 1 includes a substrate support member 10, a light irradiation member 20, a light detection member 30, moving members 40a and 40b, a controller 50, and a storage unit 60.

A substrate W, where a plurality of semiconductor devices SD are formed, is placed on substrate support member 10. Light irradiation member 20 and light detection member 30 are vertically spaced apart from substrate support member 10.

Light irradiation member 20 irradiates light to a semiconductor device SD of the substrate W placed on substrate support member 10. Light irradiation member 20 may be disposed at an incline to irradiate light onto a plane of the substrate W, at a predetermined angle. Light irradiation member 20 may include a light source (not shown) such as a semiconductor diode emitting light of a single wavelength and a lens system (not shown) for collecting light. Light detection member 30 receives light reflected from a semiconductor device SD in order to detect defects of semiconductor device SD. Light detection member 30 may be disposed at an incline in order to detect light reflected at a reflection angle corresponding to an incident angle of the light irradiated onto the plane of the substrate W. Light detection member 30 may be, for example, a photo detector such as a charge-coupled device (CCD). An electronic signal corresponding to the intensity of light reflected from a semiconductor device is generated in order to obtain image data of a surface of the semiconductor device.

Moving members 40a and 40b move substrate support member 10 in arrangement directions of the semiconductor devices SD formed at the substrate W, i.e., a first direction (I) and a second direction (II). First moving member 40a moves substrate support member 10 in first direction (I), and second moving member 40b moves substrate support member 10 in second direction (II). Light irradiation member 20 and light detection member 30 are fixed on substrate support member 10. While moving members 40a and 40b move substrate support member 10 in first direction (I) and second direction (II), light irradiation member 20 irradiates light on semiconductor devices SD.

Controller 50 controls the operations of first and second moving members 40a and 40b. From the image data that the light detection member 30 obtains, controller 50 determines whether a pattern defect (e.g., break of pattern, bridge, void, etc.) of a semiconductor device has occurred or particles have been generated. Thereafter, controller 50 transmits defect occurrence data based on positions of semiconductor devices to storage unit 60. Storage unit 60 stores the data transmitted from controller 50 and transmits the stored data to controller 50 according to a request from controller 50.

Figure 3:
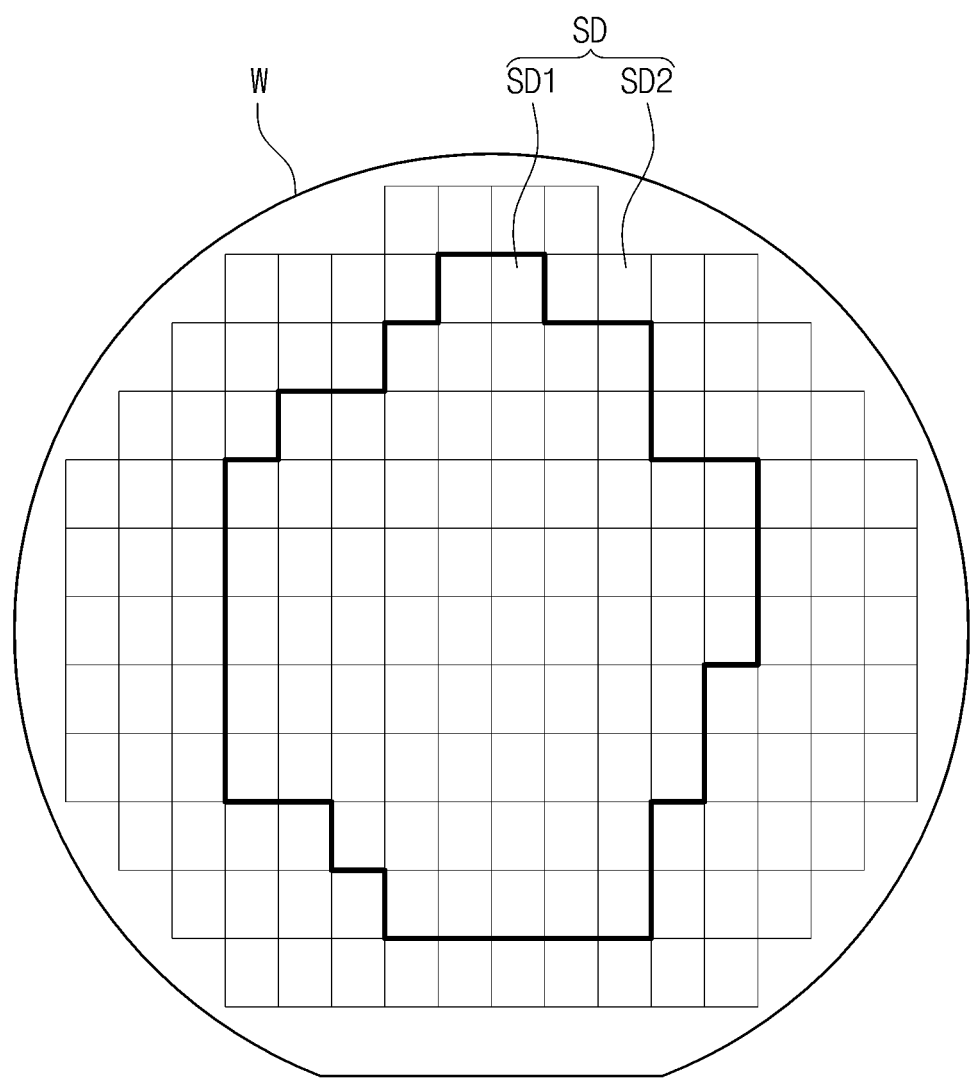
FIG. 3 is a top plan view of an inspection target substrate.

FIG. 3 is a top plan view of an inspection target substrate W. Inspection target substrate W may include semiconductor devices that are subjected to an exposure process under different exposure conditions, in order to detect more defects at the edge area than at the center area. In addition, even semiconductor devices SD1 included in the center region of the substrate W may be exposed under different exposure conditions. Similarly, even semiconductor devices SD2, included in an edge region of substrate W, may be exposed under different exposure conditions. The exposure conditions may be, for example, focal length and exposure time. A pattern is formed by developing and etching the exposed substrate. Using the substrate inspecting apparatus 1, a test is performed in order to determine whether a defect occurs at a substrate where the pattern is formed. Exposure conditions applied to semiconductor devices which have been determined through the substrate test to be less defective (i.e., good) may be applied to a practical exposure process of semiconductor devices.

Although an inspection target substrate according to this exemplary embodiment is a substrate where patterns are formed while varying exposure conditions, the inventive concept is not limited thereto. Rather, the inspect target substrate may be a test substrate for verifying conditions of other semiconductor manufacturing processes.

Figure 4:
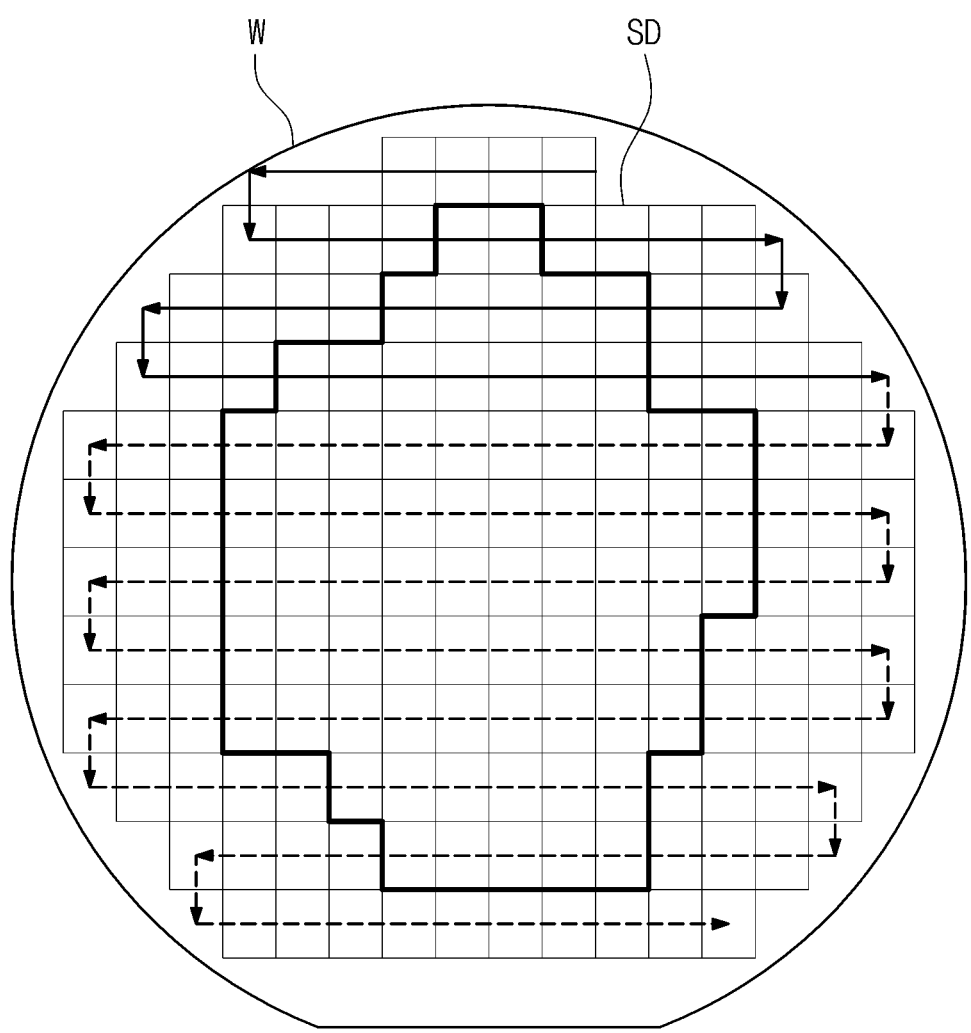
FIG. 4 illustrates a substrate inspection method which scans in a horizontal manner.
Figure 5:
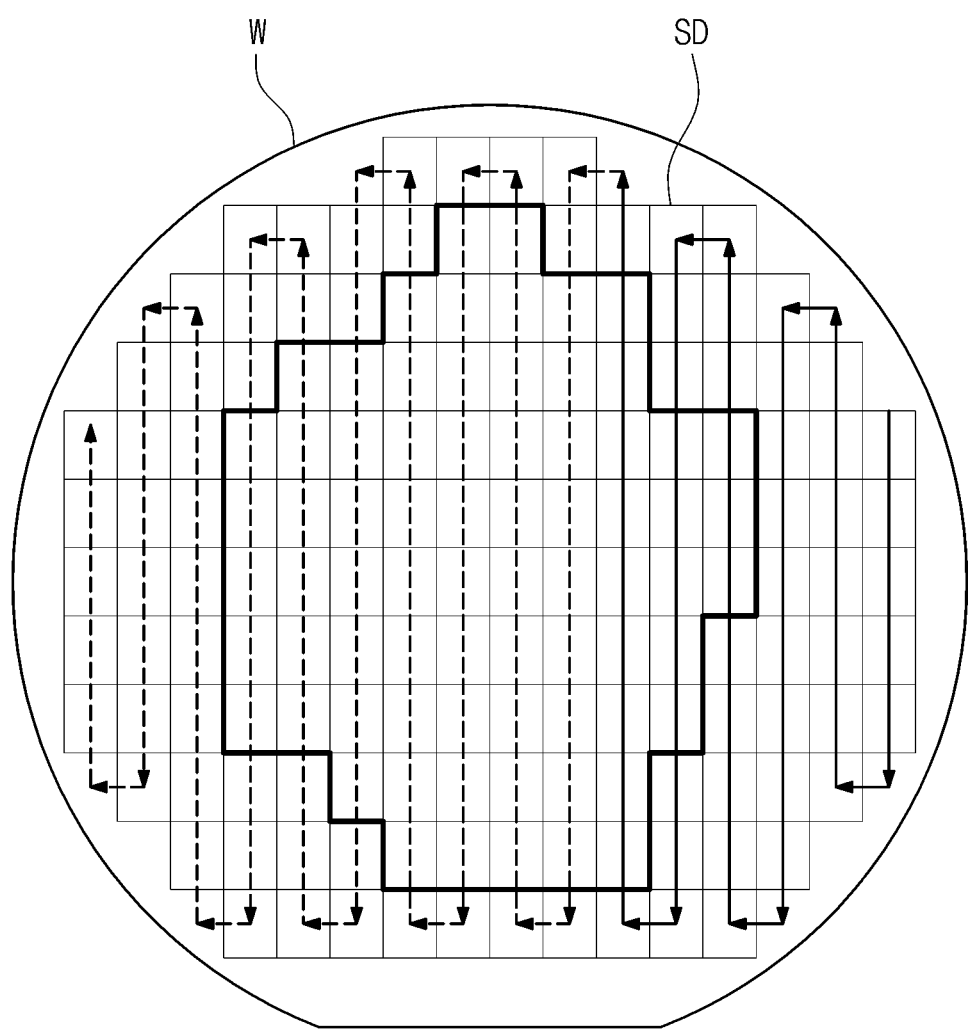
FIG. 5 illustrates a substrate inspection method which scans in a vertical manner.

FIG. 4 illustrates a substrate inspection method which scans in a horizontal manner, and FIG. 5 illustrates a substrate inspection method which scans in a vertical manner.

Referring to FIGS. 4 and 5, according to conventional substrate inspection methods, defects of a substrate W may be inspected while moving a light irradiation position by means of zigzag scanning performed in a horizontal direction, to the entire pattern surface of the substrate (see FIG. 4) or zigzag scanning performed in a vertical direction to the entire pattern surface of the substrate (see FIG. 5). In such an inspection method, before inspecting semiconductor devices in the center area of a substrate to which an exposure condition is applied, semiconductor devices in the edge area of the substrate are first inspected to detect more defects. Thus, since an excessive number of defects are detected from the semiconductor devices in the edge area of the substrate in the early stage of substrate inspection, the storage unit for storing data of defects which are detected during inspection may be overloaded and result in a shut down of the operation of the substrate inspection apparatus.

Figure 6:
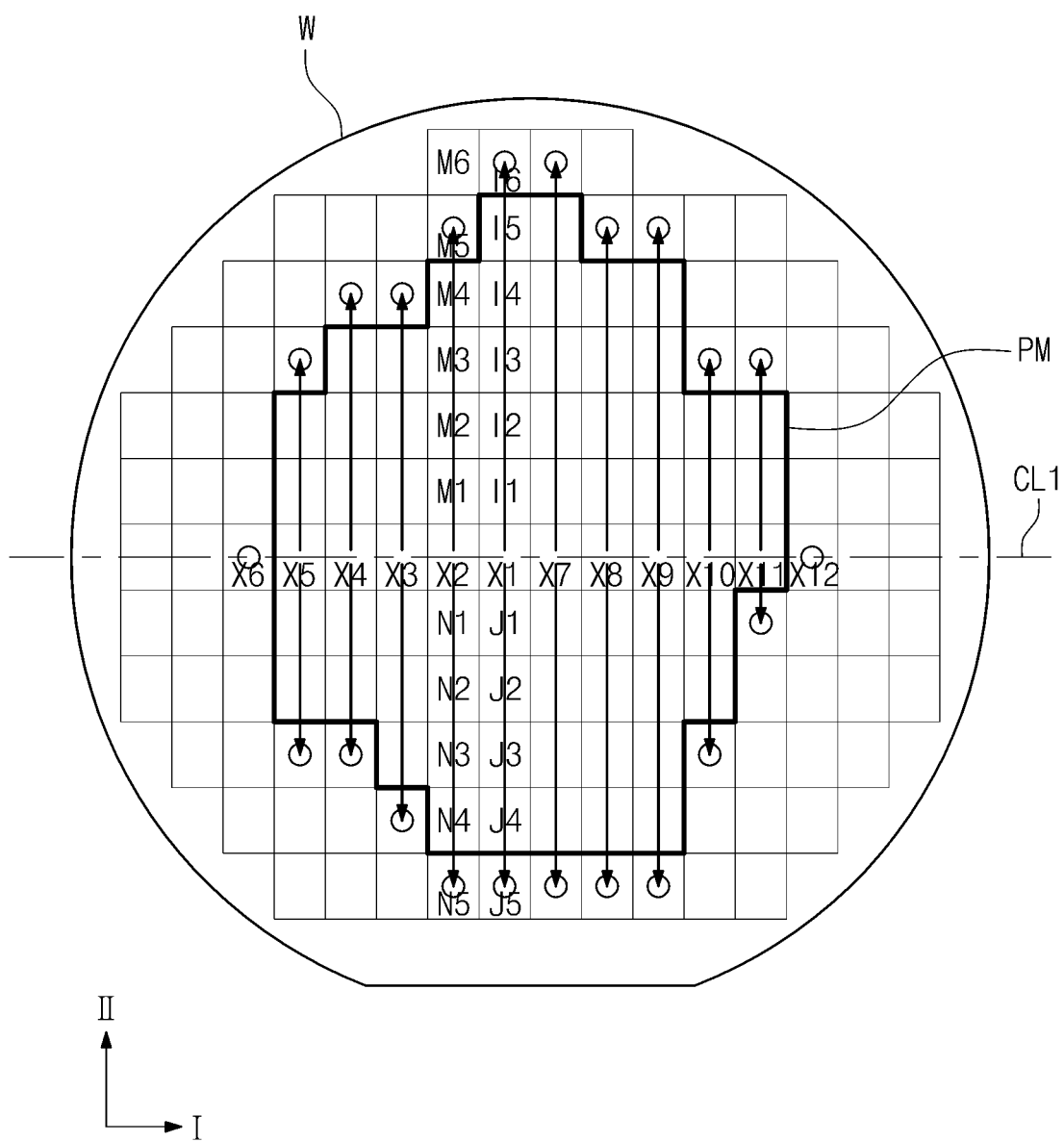
FIG. 6 illustrates an example of a substrate inspection method according to an exemplary embodiment.

FIG. 6 illustrates an example of a substrate inspection method according to an exemplary embodiment.

Referring to FIGS. 2 and 6, light irradiation member 20 irradiates light a semiconductor device SD formed on a substrate W. Light detection member 30 detects light reflected from semiconductor device SD in order to inspect a defect of semiconductor device SD. At this point, a light irradiation position of light irradiation member 20 may gradually move from a semiconductor device formed in the center area of substrate W to a semiconductor device formed in the edge area of substrate W. First and second moving members 40a and 40b move substrate support member 10 in first and second directions (I and II), which may allow a light irradiation position to move along substrate W.

The light irradiation position of light irradiation member 20 may sequentially move from respective semiconductor devices disposed on a central line CL1 of a plane of the substrate W to semiconductor devices disposed in a direction perpendicular to the center line CL1. Center line CL1 may be aligned in the first direction I among arrangement directions of semiconductor devices SD formed on substrate W.

For example, the light irradiation position may sequentially move from one semiconductor device X1 disposed in the center area on the center line CL1 from semiconductor devices I1, I2, . . . , and I6 arranged in an upward second direction (II). Upon moving the light irradiation position along the semiconductor devices I1, I2, . . . , and I6, when the number of detects of an inspected semiconductor device exceeds a predetermined value, the other semiconductor devices disposed at the outer side of the inspected semiconductor device are not inspected in the second direction. In this exemplary embodiment, although the number of defects of the semiconductor device I6 exceeds a predetermined value, the semiconductor device I6 is not inspected any longer because it is disposed at the end of a corresponding column.

Thereafter, the light irradiation position may sequentially move to semiconductor devices J1, J2, . . . , and J5 arranged in a downward second direction (II). Upon moving the light irradiation position along the semiconductor devices J1, J2, . . . , and J5, when the number of defects of an inspected semiconductor device exceeds a predetermined value, the other semiconductor devices disposed at the outside of the inspected semiconductor device are not inspected in the downward second direction (II). In this exemplary embodiment, although the number of defects of the semiconductor device J5 exceeds a predetermined value, the inspection is no longer conducted because semiconductor device J5 is disposed at the end of a corresponding column.

Thereafter, semiconductor devices are inspected while moving the light irradiation position around another semiconductor device X2 adjacent to the semiconductor device X1, on center line CL1. The light irradiation position may sequentially move from semiconductor device X2 to semiconductor devices M1, M2, . . . , and M6 arranged in the upward second direction (II). Upon sequentially moving the light irradiation position along the semiconductor devices M1, M2, . . . , and M6, when the number of defects of an inspected semiconductor devices exceeds a predetermined value, semiconductor devices disposed at the outside of the inspected semiconductor device are not inspected in the upward second direction (II). In this exemplary embodiment, since the number of defects of semiconductor device M5 exceeds a predetermined value, an inspection of semiconductor device M5 stops and an inspection of semiconductor M6 is not conducted.

Thereafter, the light irradiation position may sequentially move from semiconductor device X5 to semiconductor devices N1, N2, . . . , and N5 arranged in the downward second direction (II). Upon sequentially moving the light irradiation position along the semiconductor devices N1, N2, . . . , and N5, when the number of defects of an inspected semiconductor device exceeds a predetermined value, the other semiconductor devices disposed at the outside of the inspected semiconductor device are not inspected in the downward second direction (II). In this exemplary embodiment, although the number of defects of semiconductor device N5 exceeds a predetermined value, the inspection is not conducted any longer because semiconductor device N5 is disposed at the end of a corresponding column.

Similarly, semiconductor devices are inspected while moving the light irradiation position around semiconductor devices X3, X4, . . . , and X12 disposed at different locations along the center line CL in the second direction (II). The inspection of the semiconductor devices may be conducted at random or in the order of adjacent positions among the semiconductor devices X3, X4, . . . , and X12 along the center line CL1. In the situation regarding semiconductor devices X6 and X12, the number of their respective inspected defects exceeds a predetermined value. Therefore, the inspection is not conducted any longer in the upward or downward direction (II).

Figure 7:
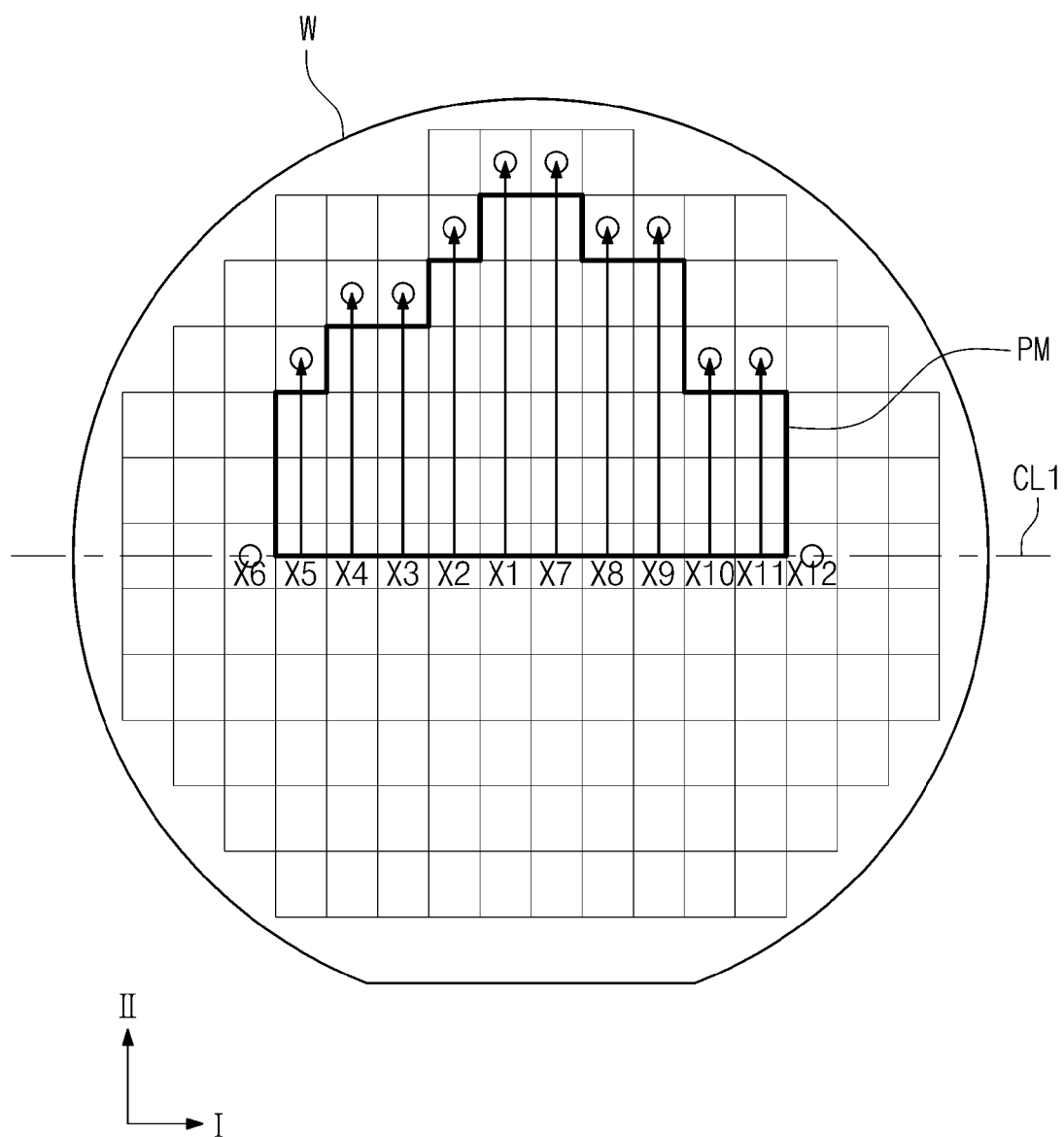
FIGS. 7 and 8 illustrate modified examples of the substrate inspection method in FIG. 6.

In FIG. 6, there has been described an example where semiconductor devices are inspected while moving a light irradiation position around semiconductor devices X1, X2, . . . , and X12 on a center line CL in an upward second direction (II) and a downward second direction (II). However, as shown in FIG. 7, semiconductor devices may be inspected while moving a light irradiation position around semiconductor devices X1, X2, . . . , and X12 only in the upward second direction (II). To the contrary, semiconductor devices may be inspected while moving a light irradiation position around semiconductor devices X1, X2, . . . , and X12 only in the downward second direction (II).

Figure 8:
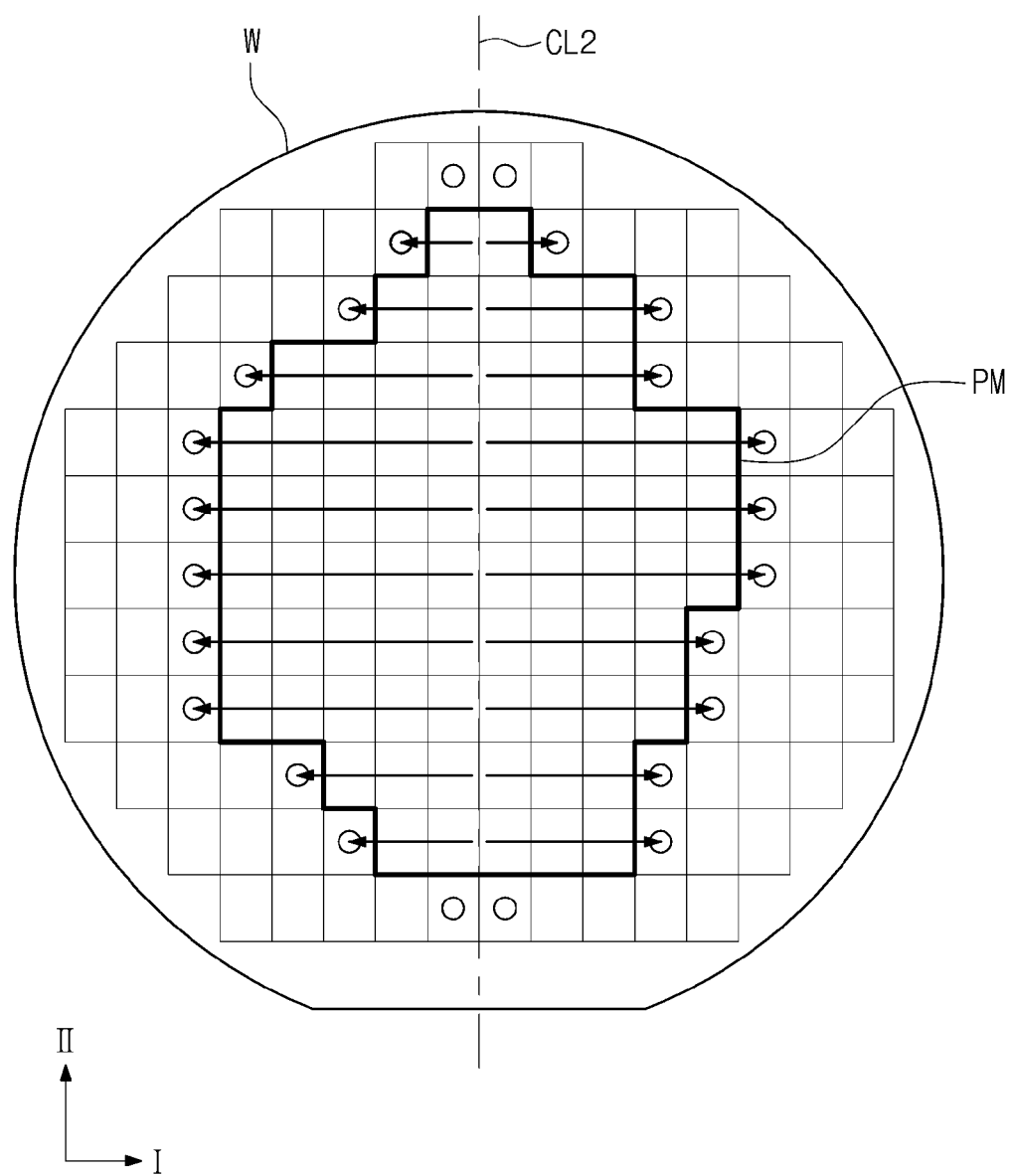

In FIG. 6, there is shown an example where the inspection is conducted in the second direction (II) around semiconductor devices X1, X2, ..., and X12 along the center line CL1 aligned in the first direction (I). But, as shown in FIG. 8, the inspection may be conducted in the first direction (I) around semiconductor devices along the center line (CL2) aligned in the second direction (II).

Figure 9:
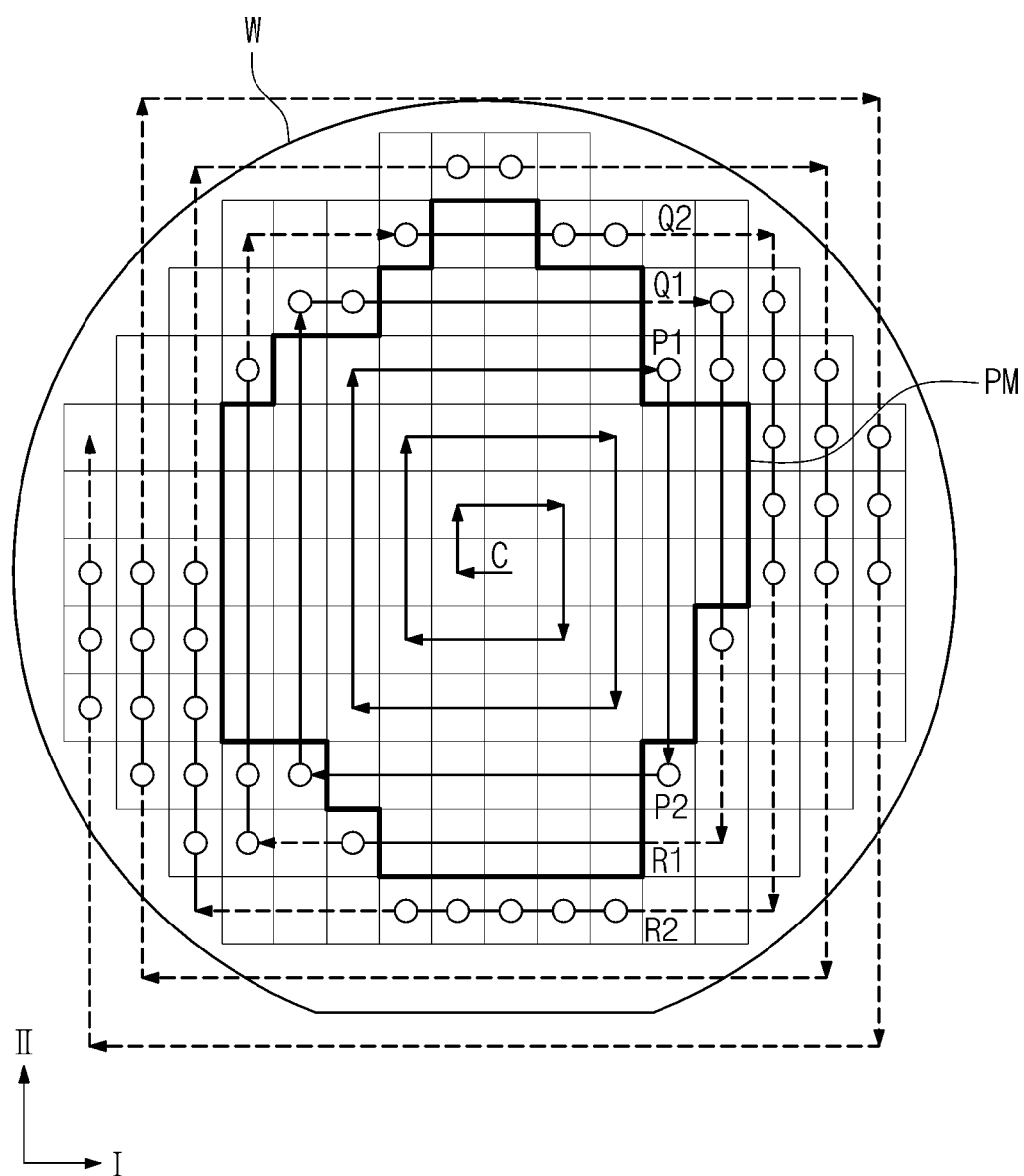
FIG. 9 illustrates another example of a substrate inspection method according to an exemplary embodiment.

FIG. 9 illustrates another example of a substrate inspection method according to an exemplary embodiment.

Referring to FIGS. 2 and 9, light irradiation member 20 irradiates light to a semiconductor device SD formed on a substrate W and detects light reflected from semiconductor device SD in order to inspect a defect of the semiconductor device SD. At this point, a light irradiation position of light irradiation member 20 may gradually move from a semiconductor device formed at a center portion of the substrate W to a semiconductor device formed at an edge portion of the substrate W. First and second moving members 40a and 40b move substrate support member 10 in first and second directions (I and II), which may allow a light irradiation position to move along the substrate W.

The light irradiation position of light irradiation member 20 may sequentially move to semiconductor devices disposed at the edge portion of substrate W while making a spiral shape, on the basis of a semiconductor device C disposed at the center of the substrate W.

When a semiconductor device P1 is determined from an inspection conducted in the same manner as described above to have defects whose number exceeds a predetermined value, location information of semiconductor device P1 is stored in storage unit 60. In subsequent steps of the inspection, semiconductor devices Q1 and Q2 disposed at the outside of semiconductor device P1 (whose location information is stored) are not inspected. The semiconductor devices Q1 and Q2 are semiconductor devices disposed around a semiconductor device P1 to be opposite to a semiconductor device C, in a direction perpendicular to a quadrangular spiral.

Similarly, when the number of inspected defects of semiconductor device P2 exceeds a predetermined value, location information of semiconductor device P2 is stored in storage unit 60. In subsequent steps of the inspection, semiconductor devices R1 and R2 disposed at the outside of the semiconductor device P2 are not inspected. The semiconductor devices R1 and R2 are semiconductor devices, disposed around a semiconductor device P2 which is opposite to the semiconductor device C, in a direction perpendicular to the quadrangular spiral.

When semiconductor devices on the substrate W are inspected in such a manner, semiconductor devices denoted by circles and semiconductor devices passed through by solid lines are inspected while semiconductor devices passed through by dotted lines are not inspected.

When a substrate is inspected by means of the above-described method, the inspection is not conducted to semiconductor devices in a substrate edge area where an excessive number of defects occur. Therefore, the time required for inspecting the substrate may be reduced. Moreover, overload of a storage unit resulting from an excessive detection of defects may be avoided in order to achieve automation of a substrate inspection apparatus.

As shown in FIGS. 6 and 9, an area PM of semiconductor devices determined to be less defective (i.e., good) is confirmed. Exposure conditions applicable to a semiconductor manufacturing process may be confirmed from exposure conditions applied to the area PM.

While the inventive concept has been particularly shown and described with reference to exemplary embodiments thereof, it will be apparent to those of ordinary skill in the art that various changes in form and detail may be made therein without departing from the spirit and scope of the inventive concept as defined by the following claims.

What is claimed is:

1. A method for inspecting a substrate, comprising:
   irradiating light to a semiconductor device formed on a substrate; and
   detecting light reflected from the semiconductor device in order to inspect the semiconductor device for defects,
   wherein an irradiation position of the light gradually moves from a semiconductor device formed at the center of the substrate to a semiconductor device formed on an edge of the substrate, and
   wherein when the number of defects of the inspected semiconductor device exceeds a predetermined value, other semiconductor devices disposed outside of the inspected semiconductor device stop being inspected in a moving direction of the irradiation position of the light.

2. The method as set forth in claim 1, wherein
   the irradiation position of the light sequentially moves from a semiconductor device disposed along a center line of a plane of the substrate to semiconductor devices in a direction perpendicular to the center line.

3. The method as set forth in claim 2, wherein
   the center line is aligned in one of a plurality of arrangement directions of the semiconductor devices formed on the substrate.

4. The method as set forth in claim 3, wherein
   the substrate includes semiconductor devices where patterns are formed in different exposure conditions in order to detect more defects at the center portion of the substrate than at the edge portion of the substrate.

5. The method as set forth in claim 1, wherein
   after stopping inspection of the other semiconductor devices outside of the inspected semiconductor device, the irradiation position of the light moves from another semiconductor device disposed along the center line to semiconductor devices disposed in a direction perpendicular to the center line.

6. The method as set forth in claim 1, wherein
   the irradiation position of the light sequentially moves from a central semiconductor device disposed at the center of the substrate to semiconductor devices disposed on the edge of the substrate while making a quadrangular spiral.

7. The method as set forth in claim 6, wherein
   location information of a semiconductor device whose inspected defects are greater than a predetermined value is stored, and
   semiconductor devices disposed around the semiconductor device to be opposite to the semiconductor device whose location information is stored are not inspected in one of horizontal and vertical directions of the quadrangular spiral.

8. The method as set forth in claim 7, wherein
   the substrate includes semiconductor devices where patterns are formed under different exposure conditions in order to detect more defects at the edge portion of the substrate than at the center portion of the substrate.

9. A method for inspecting a substrate, comprising:
   providing a substrate including semiconductor devices arranged in the form of lattice and where patterns are formed under different exposure conditions such that more defects are detected at an edge portion of the substrate than at a center portion of the substrate;

sequentially irradiating light from a semiconductor device formed at the center portion of the substrate to a semiconductor device formed at the edge portion of the substrate; and detecting light reflected from the semiconductor devices to inspect defects of the semiconductor devices, wherein when the number of defects of the inspected semiconductor device exceeds a predetermined value, other semiconductor devices disposed outside of the inspected semiconductor device stop being inspected in a moving direction of an diation position of the light.

10. The method as set forth in claim 9, wherein
the light is irradiated from the respective semiconductor devices linearly disposed in a first direction from among the arrangement directions of the semiconductor devices to the semiconductor devices disposed in a second direction.

11. The method as set forth in claim 10, wherein
the inspection is conducted from the semiconductor device disposed at the center of the substrate, among the semiconductor devices linearly disposed in the first direction, to the semiconductor device disposed around the semiconductor device.

12. The method as set forth in claim 9, wherein
the light is sequentially irradiated from a central semiconductor device disposed at the center of the substrate to semiconductor devices disposed on the edge of the substrate while making a quadrangular spiral.

13. The method as set forth in claim 12, further comprising:
location information of the semiconductor device whose inspected defects are greater than a predetermined value is stored, and semiconductor devices disposed around the semiconductor device in order to be opposite from the semiconductor device whose location information is stored are not inspected in one of horizontal and vertical directions of the quadrangular spiral.

* * * * *